United States Patent [19]
Brown et al.

[11] Patent Number: 5,364,982
[45] Date of Patent: Nov. 15, 1994

[54] CATALYTIC HYDROXYLATION OF PHENOL

[75] Inventors: Scott W. Brown, Wigan; Anthony Hackett, Warrington; Angela M. King, Netherton; Alexander Johnstone, South Wirral; William R. Sanderson, Warrington, all of United Kingdom

[73] Assignee: Solvay Interox Limited, Warrington, England

[21] Appl. No.: 94,210

[22] PCT Filed: Feb. 13, 1992

[86] PCT No.: PCT/GB92/00258

§ 371 Date: Aug. 3, 1993

§ 102(e) Date: Aug. 3, 1993

[30] Foreign Application Priority Data

Feb. 16, 1991 [GB] United Kingdom ............... 91033.3
Jan. 16, 1992 [GB] United Kingdom ............. 9200929.9

[51] Int. Cl.$^5$ .................................................. C07C 37/60
[52] U.S. Cl. ..................................... 568/771; 568/741; 568/800; 568/803
[58] Field of Search ................ 568/741, 771, 803, 800

[56] References Cited

FOREIGN PATENT DOCUMENTS 0338666 10/1989 European Pat. Off. .
14691 9/1992 WIPO .

OTHER PUBLICATIONS

Shimizu, et al., "A Convenient Synthesis of Alkyl-Substituted P-Benzoquinones from Phenols by a H2O2/Heteropolyacid System", Tetrahedron Letters, vol. 30, No. 4, 1989, pp. 471–474.

Takamitsu, et al., Chemical Abstracts, vol. 87, No. 25, 19 Dec. 1977, Abstract No. 201076Z, "Dihydric Phenols", p. 686, Col. 1.

*Primary Examiner*—Werren B. Lone
*Attorney, Agent, or Firm*—Larson and Taylor

[57] ABSTRACT

Hydroxylation of phenol is prone to the production of tarry by-products. Selective hydroxylation of phenol can be obtained by reacting a limited amount of hydrogen peroxide with phenol in solution in a compatible organic solvent and in the presence of a catalyst that is at least partly soluble in the reaction medium and is the salt of a heteropolyacid of general formula: i) $Q_3PMo_mW_{12-m}O_{40}$ or ii) $Q_{3+v}PM_nV_vO_{40}$, in which Q represents a compatible organic cation, m is zero or an integer less than 6, M represents molybdenum or tungsten, v is an integer which is up to 3, and n is an integer such that $n+v=12$. A preferred organic cation comprises cetyl pyridinium. Selectivity towards catechol is particularly observed employing heteropolyacid salts in which $m=0$ in formula i) and when $n=11$ and M=tungsten in formula ii) and towards hydroquinone when $n=11$ and M=molybdenum in formula ii). Preferably the reaction medium comprises acetonitrile.

15 Claims, No Drawings

CATALYTIC HYDROXYLATION OF PHENOL

The present invention relates to a process for the hydroxylation of phenol.

Phenol is a readily available raw material which can be hydroxylated using aqueous hydrogen peroxide and a catalyst to produce dihydric phenols, and particularly mixtures containing hydroquinone and catechol. However, two factors should be taken into account when seeking to hydroxylate phenol. First, the introduction of a second hydroxyl substituent onto the aromatic nucleus tends to activate the molecule towards further reaction and this leads to the formation of a mixture of unwanted tarry by-products. Self-evidently it would be desirable to hydroxylate selectively, i.e. favour dihydric phenol formation compared with tarry by-product formation. Secondly, hydroquinone and catechol tend to be used for different purposes. For example, hydroquinone is a photographic developer and catechol is an intermediate in the production of industrial anti-oxidants. Consequently, it remains an aim of producers to obtain one or other product selectively.

A commercial process has been developed for hydroxylating phenol based upon catalysed hydrogen peroxide which tends to produce mixtures containing a major fraction of catechol, but additionally a minor, significant fraction of hydroquinone, typically in a mole ratio of about 3:1. The proportion of tarry by-products has been controlled by limiting very strictly to the use of very low mole ratios of hydrogen peroxide to phenol, but inevitably this restricts the extent of conversion of the phenol and hence the space yield of the plant.

European Patent Application, Publication No 0 338 666A, inventors M Shimizu et al, describes a process in which a tri-alkyl substituted phenol is converted to the corresponding tri-alkyl benzoquinone using hydrogen peroxide and a heteropolyacid catalyst. The inventors Shimizu et al have applied a similar process to a wider range of alkyl-substituted phenol substrates and described the results obtained in a paper entitled "A convenient synthesis of alkyl-substituted p-benzoquinones from phenols by a $H_2O_2$/heteropolyacid system", published in Tetrahedron Letters, vol 30, No 4, pp471–474. These two publications teach that alkyl substituted phenols are converted through to the corresponding benzoquinone rather than selectively to an hydroxylated product. The only teaching regarding phenol itself was that it gave only a trace amount of p-benzoquinone. Accordingly, neither publication provides any clear teaching on how to hydroxylate phenol selectively.

It is an objective of the present invention to identify more exactly the conditions in which any one or more of the disadvantages in the aforementioned commercial process can be ameliorated or overcome.

According to the present invention, there is provided a process for the hydroxylation of phenol in which phenol is dispersed in a compatible organic reaction medium and brought into contact with hydrogen peroxide in the presence of a catalyst characterised in that the catalyst, which is at least partly soluble in the reaction medium, is selected from salts of heteropolyacids of general formula i) $Q_3 PMo_m W_{(12-m)} O_{40}$ or
ii) $Q_{3+v} PM_n V_v O_{40}$ in which Q represents a compatible organic cation, m is zero or an integer less than 6, M represents molybdenum or tungsten, v is an integer which is up to 3, and n is an integer such that $n+v=12$ and no more than a limited amount of hydrogen peroxide is employed.

In British Patent Application no 9103323.3, filed on 16th Feb. 1991 from which priority is claimed, the use was described of certain catalysts for selective phenol hydroxylation obeying the general formula:

$$Q_3 PMo_n W_{(12-n)} O_{40}$$

in which Q represents a compatible organic cation and n is an integer which is less than or greater than 6. Herein, such catalysts when n is less than 6 are represented by general formula i, in which it will be observed that m has been substituted for n. Subsequent analysis of the catalyst tested in support of the formula in which n was greater than 6 showed that the anion in HPS11 had the formula $PMo_{11}VO_{40}$, i.e. contained vanadium as a hetero metal atom rather than tungsten. The use of such catalysts in which n has a high value together with related catalysts was described in British Patent Application No 9200929.9 to the same applicants from which priority is also claimed. Such catalysts are described herein with reference to formula ii.

By selecting the salt of the selected heteropolyacids, it has been found that hydroxylation of phenol can occur to a significantly greater extent than when the same heteropolyacid in acidic form was employed, the latter in extreme cases being unable to promote any significant amount of hydroxylation. Alternatively, the salt can promote a significantly improved selectivity of conversion of the phenol to a particular dihydric phenol, compared with use of the acid form of catalyst under otherwise the same reaction conditions.

By selecting the composition of the heteropolyacid catalyst in accordance with the description provided herein, it has been found possible, particularly in conjunction with the selection of the organic reaction medium, to observe not only selective hydroxylation of phenol to dihydric phenols, but also hydroxylation having a substantial degree of selectivity towards a specific dihydric phenol, being either hydroquinone or catechol.

The organic cation Q is desirably an onium cation and particularly an ammonium or phosphonium cation. It is preferable to select a cation that is commensurate in size with the heteropolyacid anion, to at least a reasonable extent. In accordance therewith, it is particularly suitable for the cation to contain at least 8 carbon atoms and preferably from about 15 to about 30 carbons. The carbons may be distributed evenly as for example in tetra ethyl or tetrabutyl ammonium or one or two of the alkyl substituents can contain a disproportionate number of carbons, as in a long chain substituent of from e.g. 9 to 18 carbons with the remaining alkyl substituents being short chain, such as ethyl of methyl. Two or more of the alkyl substituents can combine to form with the hereto atom, e.g. nitrogen, a heterocycle, such as pyridinium. An especially convenient range of onium cations comprises alkyl pyridinium cations in which the alkyl contains from 12 to 18 linear carbons, such as cetyl pyridinium.

The choice of heteropolyacid anion is of importance in directing hydroxylation selectively towards either hydroquinone or catechol. Such a choice can be made on the basis of analysis of the products obtained in a small scale trial of each heteropolyacid anion employing conditions according to the present invention. It has been found in the present investigations that in trials employing a heteropolyacid anion in which n=11 in formula ii, when the metal was molybdenum, some selectivity towards the production of hydroquinone was observed and towards catechol when the metal was tungsten. Likewise, when m=0 in formula i), i.e. tungsten but no molybdenum was present, some selectivity towards the production of hydroquinone was also observed. In comparison trials which employed a salt of a heteropolyacid in which n=6 and M=tungsten, i.e. a process not according to the present invention, no selectivity towards dihydric phenol production was observed, let alone selectivity towards a particular dihydric phenol.

It will be understood that the catalyst is described herein in terms of the heteropolyacid salt that is introduced into the reaction mixture, and that during the reaction period, a fraction of the heteropolyacid may become transformed in situ to species different from that introduced. The present invention specifically includes the use of any active species which is so derived in situ, even if that species does not accord with the general formulae given hereinabove.

It is desirable to choose a suitable temperature at which to carry out the hydroxylation reaction. The temperature selection takes into account the need to dissolve phenol and at least a proportion of the heteropolyacid catalyst in the reaction medium. In practice it has been found that a temperature in the vicinity of at least 40° C. is advantageous. The upper limit comprises the reflux temperature for medium, which naturally varies depending upon the chemical nature of that medium. In practice, the reaction is often effected at a temperature of from 50° to 80° C. In many operational embodiments, the amount of catalyst is such that it is completely dissolved when the reaction is conducted at a temperature of at least 50° C.

A suitable solvent in which the reaction can be carried out has been found to include low molecular weight aliphatic carboxylic acids, including in particular acetic acid. A preferred class of solvents comprises low molecular weight nitriles and in particular acetonitrile. Such a class of solvent is preferred in that it includes the best solvent of those tested as regards optimising the selectivity of the reaction towards, for example, hydroquinone as predominant product. Mixtures of the two aforementioned classes of solvent can be employed.

One especially desirable combination of catalyst, solvent and reaction temperature comprises the use of a salt in which the cation is a C10 to C18 pyridinium ion and the anion contains tungsten or especially molybdenum in a very high ratio to vanadium, such as about 11:1, the solvent comprises acetonitrile as the major proportion and the temperature is from 50° to 80° C.

One factor of importance in conducting this reaction appears to comprise the amount or proportion of water present in the reaction medium. It is inevitable that some water will be present not only because the latter is a reaction product and a decomposition product of hydrogen peroxide but also because water is the diluent in current commercial grades of hydrogen peroxide. In general, the amounts of water introduced or generated by the use of commercial concentrated hydrogen peroxide can be tolerated, such as those containing at least 35% and especially from 50 to 70% w/w $H_2O_2$.

It has been found that it is desirable to avoid introducing or employing an excessive amount of water, particularly when using a molybdenum-rich heteropolyacid salt as catalyst. For such catalysts, it is advantageous to avoid the introduction of further water as part of the reaction medium, though some advantage can be retained even if water comprises up to 2/3rds approximately by volume of the solvents employed. It has been observed when using a salt of a heteropolyacid that is molybdenum-rich (e.g. n=11), that introduction of additional water beyond that present in concentrated hydrogen peroxide promotes catechol production. This thereby impairs somewhat the selectivity of hydroquinone product formation, although overall the selectivity towards the total dihydric phenol production remains.

When employing a salt of a tungsten-rich heteropolyacid, such as the vanadium-free heteropolyacids of formula i), e.g. those in which m=0, the presence of additional water has likewise been observed to boost catechol formation. However, for such tungsten-rich salts, it may even be beneficial, in that in a number of trials it has been seen to reinforce the tendency of the tungsten-rich catalyst to produce a significant proportion of catechol, thereby improving selectivity. Thus, when using such a salt, it is convenient to employ a significant fraction of water in the solvent; such a fraction is from about 1/3rd to about 4/5ths water, though selected such that the solvent mixture remains as a single phase.

The best results according to the present invention have been obtained when phenol had been converted in a proportion of from about 5 to 20% and preferably from about 10 to about 15%. Accordingly, in one most desirable aspect of the invention, the reagents are preferably selected so as to achieve such a conversion or the reaction quenched when monitoring of the reagents and products indicates that a conversion in that range has been attained.

It is desirable, in processes according to the present invention, to employ at least 0.01 mmole and up to 100 mmole of catalyst salt per mole of phenol, and preferably from 0.1 to 5 mmole per mole of phenol. In some processes, it has been convenient to employ phenol significantly in a weight excess to catalyst, such as at least 2.5:1 and significant yields of dihydric phenols have been obtained using a phenol:catalyst weight ratio selected in the range of from 5:1 to 15:1.

The concentration of phenol is normally selected within the range of 0.1 to 2 moles per liter, taking into account such factors as the temperature and composition of the reaction medium.

One other variable comprises the mole ratio of hydrogen peroxide to phenol. In processes according to the present invention, no more than a limited amount of hydrogen peroxide is employed, with the specific intention of reducing the extent to which over-oxidation of phenol may occur. Generally, it is desirable to restrict the ratio of hydrogen peroxide:phenol to about 4:1 or less. It will be recognised that this amount is substantially less than the amount of hydrogen peroxide advocated in the patent application and paper by Shimizu referred to hereinbefore. Significant yields of dihydric phenols have been obtained when the mole ratio of peroxide consumed to phenol present initially fell in the range of from about 1:1 to about 2:1. Unreacted phenol may be recovered from the reaction medium and employed in a subsequent reaction. It will be recognised that the lower preferred limit for hydrogen peroxide:phenol will depend at least partly upon the extent to which a user is willing to recycle unreacted phenol. It is preferable for at least 5% phenol to be reacted in each cycle.

In practice, the present invention is carried out for reasons of convenience and safety by forming a solution of phenol and the catalyst in the selected reaction medium at the selected reaction temperature and thereafter introducing the selected amount of hydrogen peroxide solution over a significant introduction period, preferably gradually. A convenient peroxide introduction period is often chosen from the range of 15 to 75 minutes. Thereafter, it is desirable for the reaction mixture to be maintained with agitation at the reaction temperature for a further reaction period such that the overall period of introduction and reaction is from about 2 to 7 hours.

Having described the present invention in a general way, specific embodiments thereof are described hereinafter in greater detail by way of example only.

In the Comparisons and Examples, the catalyst HPA0 was available commercially and catalysts HPS0, HPS6, HPA11, HPS11, HPS9, HPS10, HPWA11 and HPWS11 were all made in accordance with the process disclosed by Y Matoba et al in Synthetic Communications, 14, p865 (1984) for respectively a heteropolyacid or salt thereof. They were characterised as follows:

| Catalyst | cation | anion |
|---|---|---|
| HPA0 | H | $PW_{12}O_{40}$ |
| HPS0 | cetyl pyridinium | $PW_{12}O_{40}$ |
| HPS6 | " | $PMo_6W_6O_{40}$ |
| HPA11 | H | $PMo_{11}VO_{40}$ |
| HPS11 | cetyl pyridinium | $PMo_{11}VO_{40}$ |
| HPS9 | " | $PMo_9V_3O_{40}$ |
| HPS10 | " | $PMo_{10}V_2O_{40}$ |
| HPWA11 | H | $PW_{11}VO_{40}$ |
| HPWS11 | cetyl pyridinium | $PW_{11}VO_{40}$ |

Although the catalysts HPS9 and HPS10 had the approximate stoichiometry indicated, it is believed that they may contain a mixture of anions including the designated species and $PMo_{11}VO_{40}$.

Examples using HPS0, HPS11, HPS9, HPS10 and HPWS11 are according to the invention and processes using HPA0, HPS6 and HPA11 are included by way of comparison.

COMPARISONS C1 TO C4

In these Comparisons, trials were conducted to determine if the catalyst described in the aforementioned European Patent Application listing Shimizu et al as inventors would cause hydrogen peroxide to react with phenol at the reaction temperature and mole ratio of peroxide to phenol specified therein to produce selectively a dihydric phenol product. In each of these Comparison trials, a three necked round bottom flask of 25 ml capacity, equipped with a magnetic stirrer, thermometer, condenser and inlet tube for hydrogen peroxide was charged phenol (0.2 g, 2 mmole), solvent (10 ml) and catalyst (HPA0 or HPS11). The contents of the flask were brought to a temperature of 30° C. in a water bath and hydrogen peroxide, (35% solution w/w, 40 mmole) was introduced gradually into the stirred mixture over a period of 45 minutes using a peristaltic pump. The reaction was permitted to continue for a further 5 hours at the same temperature. The reaction mixture was analysed by reverse phase HPLC employing silica coated with ODS as the stationary phase and either 2% acetic acid in acetonitrile or 2% aqueous acetic acid as the eluant. Residual hydrogen peroxide, if any, was determined by potassium iodide/sodium thiosulphate titration.

The conditions and results are summarised in Table 1 below. In these Comparisons and subsequent Examples, "Product Yield" means the molar percentage obtained of the specified dihydric phenol product, based on phenol introduced at the start of the reaction, "para" indicates hydroquinone, "ortho" indicates catechol and "Conversion of phenol" means the molar percentage of phenol that has been consumed during the reaction, unless otherwise stated. A "—" indicates that a trace at most was produced or converted, depending on the context.

TABLE 1

| Solvent | Catalyst | Mole Ratio phenol:H2O2 | Product Yield para | Product Yield ortho | Conversion of phenol |
|---|---|---|---|---|---|
| C1 | AcOH HPA0 | 1:20 | — | — | 17.0 |
| C2 | MeCN HPA0 | 1:20 | — | — | — |
| C3 | AcOH HPS11 | 1:20 | — | — | 15.0 |
| C4 | MeCN HPS11 | 1:20 | — | — | 6.8 |

From Table 1, Comparisons C1 and C2, it can be seen that no significant amounts of dihydric phenol were produced from phenol using the process conditions and catalyst of Shimizu et al, viz a low reaction temperature, substantially greater than a limited amount of hydrogen peroxide and using HPA0. Some phenol was converted when the solvent was acetic acid, but when the acetonitrile was selected as solvent, no significant conversion of phenol occurred. This indicates that catalyst HPA0, which was in the acidic state was unable to promote any reaction between hydrogen peroxide and phenol in acetonitrile, let alone a controlled reaction to generate a dihydric phenol. From Comparisons C3 and C4, it can be seen that under the same process conditions, a related catalyst, introduced as a salt, HPS11, was likewise unable to generate a significant amount of a dihydric phenol in either solvent, although a minor conversion of phenol was observed.

COMPARISONS C5, C8, C9, C13 AND C15; EXAMPLES 6, 7, 10 TO 12 AND 14

In these Examples and Comparisons, trials were conducted to see if the invention catalysts and the compounds in acid form could promote dihydric phenol formation under conditions different from those described by Shimizu.

In each of these Examples and Comparisons, a 100 ml three necked round bottomed flask, equipped with a magnetic stirrer, condenser, thermometer and peroxide inlet tube was charged with phenol (2.0 g, 21.3 mole), solvent (40 ml) and catalyst (0.2 g). The flask contents were then heated to 70° C. using a water bath and maintained at that temperature throughout the reaction period. Hydrogen peroxide was introduced continuously over a period of 45 minutes to attain the specified mole ratio to phenol and the reaction mixture was permitted to react for a further 5 hours. The resultant reaction mixture was analysed by the method described for Comparisons C1/2. Reaction variables and the results are summarised in Table 2 below.

TABLE 2

| Solvent | Catalyst | | Mole Ratio phenol:H$_2$O$_2$ | Product Yield | | Conversion of phenol |
|---|---|---|---|---|---|---|
| | | | | para | ortho | |
| C5 | AcOH | HPA0 | 1:2 | 1.6 | — | 40.1 |
| Ex6 | AcOH | HPS0 | 1:2 | — | 5.8 | 39.3 |
| Ex7 | AcOH | HPS11 | 1:2 | 5.6 | — | 22.8 |
| C8 | MeCN | HPA0 | 1:2 | — | — | — |
| C9 | MeCN | HPS6 | 1:2 | — | — | 5.3 |
| Ex10 | MeCN | HPS0 | 1:2 | — | 1.7 | 11.6 |
| Ex11 | MeCN | HPS11 | 1:2 | 11.7 | — | 12.2 |
| Ex12 | MeCN/H$_2$O | HPS0 | 1:2 | — | 4.1 | 22.3 |
| C13 | MeCN | HPA11 | 1:2 | 0.65 | — | 8.8 |
| Ex14 | MeCN | HPWS11 | 1:2 | — | 3.5 | 6.1 |
| C15 | MeCN | HPWA11 | 1:2 | — | — | 22.5 |

From Table 2, it can be seen that under the different conditions of the present invention, hydroxylation of phenol was promoted with the catalysts that were in salt form, viz HPS0, HPS11 and HPWS11, except for HPS6, but to a much lesser or nil extent using the same catalysts in hydrogen form, viz HPA0, HPA11 and HPWA11. When heteropolyacid salt HPS11 was employed, i.e. that which was rich in molybdenum, improved hydroxylation of phenol to hydroquinone (1,4-dihydroxybenzene) was observed. When heteropolyacid salt HPWS11 or HPS0 was employed, i.e. that which was rich in tungsten, selective hydroxylation of phenol to catechol (1,2-dihydroxybenzene) was observed.

Ex11 demonstrated a particularly effective combination of process conditions and catalyst, in that the process resulted not only in a high selectivity of conversion of phenol to dihydric phenols, but also indicated a high selectivity to the production of one specific dihydric phenol, hydroquinone.

EXAMPLES 16 TO 19

In these Examples, a number of further trials were conducted in which Example 11 was repeated, but employing a number of variations which are summarised in Table 3 below, together with the results of the trials. In Ex16, the volume ratio of MeCN to H$_2$O was 15:25.

TABLE 3

| | Phenol (g) | Solvent | Catalyst (g) | Mole Ratio phenol:H$_2$O$_2$ | Reaction Temp °C. |
|---|---|---|---|---|---|
| Ex16 | 3.0 | MeCN | HPS11 0.4 | 1:2 | 60 |
| Ex17 | 3.0 | MeCN | HPS11 0.2 | 1:1 | 60 |
| Ex18 | 2.0 | MeCN | HPS11 0.4 | 1:1 | 80 |
| Ex19 | 3.0 | MeCN/H$_2$O | HPS11 0.2 | 1:2 | 80 |

| | Reaction Period (hr) | Yield Product | | Conversion of phenol |
|---|---|---|---|---|
| | | para | ortho | |
| Ex16 | 2 | 8.9 | 1.0 | 15.1 |
| Ex17 | 4 | 1.8 | 1.7 | 6.3 |
| Ex18 | 4 | 6.3 | 1.6 | 21.9 |
| Ex19 | 4 | 10.0 | 1.7 | 11.6 |

From Table 3, it can be seen that the catalyst/solvent system was able to function in a range of process conditions and still yield significant proportions of dihydric phenol products.

EXAMPLES 20 AND 21

In these Examples, the process of Example 11 was repeated, but using respectively catalyst HPS9 and HPS10. The results are summarised in Table 4.

TABLE 4

| Solvent | Catalyst | Mole Ratio phenol:H2O2 | Product Yield | | Selectivity to phenol |
|---|---|---|---|---|---|
| | | | para | ortho | |
| Ex20 MeCN | HPS9 | 1:2 | 2.1 | — | 15.8 |
| Ex21 MeCN | HPS10 | 1:2 | 5.5 | — | 18.9 |

The results in Table 4 confirm that the catalysts containing a high ratio of molybdenum to vanadium direct the reaction towards hydroquinone rather than catechol.

We claim:

1. In a process for the hydroxylation of phenol which comprises reacting phenol with hydrogen peroxide in a compatible organic reaction medium in the presence of a catalyst to produce a dihydric phenol, the improvement wherein the catalyst, which is at least partly soluble in the reaction medium, is selected from salts of heteropolyacids of the formula
   i) $Q_3 PMo_mW_{12-m}O_{40}$, or
   ii) $Q_{3+v} PM_nV_vO_{40}$ in which Q represents a compatible organic cation, m is zero or an integer less than 6, M represents molybdenum or tungsten, v is an integer which is up to 3, and n is an integer such that n+v=12, and wherein not more than a limited amount of hydrogen peroxide is employed.

2. A process according to claim 1 wherein n=1 in formula ii) for the heteropolyacid.

3. A process according to claim 1 wherein the compatible cation Q is an onium cation containing at least 8 carbon atoms.

4. A process according to claim 3 characterised in that the onium cation comprises an alkyl pyridinium cation, preferably in which the alkyl group contains from 12 to 18 linear carbon atoms.

5. A process according to claim 1 wherein the reaction medium comprises a low molecular weight aliphatic carboxylic acid.

6. A process according to claim 1 wherein the reaction medium comprises a low molecular weight aliphatic nitrile.

7. A process according to claim 1 wherein the amount of hydrogen peroxide introduced into the reaction mixture is in a mole ratio to phenol selected within the range of about 4:1 or less.

8. A process according to claim 7 wherein the amount of hydrogen peroxide introduced into the reaction mixture is in a mole ratio to phenol selected in the range of 1:1 to 2:1.

9. A process according to claim 1 wherein the concentration of hydrogen peroxide introduced into the reaction mixture is no lower than 35%, including any water already present in the reaction mixture, when the catalyst comprises the salt of a tungsten-rich heteropolyacid.

10. A process according to claim 1 wherein the reaction medium comprises from 1/3rd to about 4/5th parts by volume of water when the catalyst comprises the salt of a molybdenum-rich heteropolyacid.

11. A process according to claim 1 wherein the reaction is terminated when from 10% to 15% of the phenol has reacted.

12. A process according to claim 1 wherein the reaction temperature is selected in the range of from 50° to 80° C.

13. In a process for the hydroxylation of phenol which comprises reacting phenol with hydrogen peroxide in a compatible organic reaction medium in the presence of a catalyst to produce a dihydric phenol, the improvement wherein the catalyst, which is at least partly soluble in the reaction medium, is selected from salts of heteropolyacids of the formula i) $Q_3PW_{12}O_{40}$, or ii) $Q_{3+v}PM_nV_vO_{40}$ in which Q represents a compatible organic cation, m is zero or an integer less than 6, M represents molybdenum or tungsten, v is an integer which is up to 3, and n is an integer such that $n+v=12$, and wherein not more than a limited amount of hydrogen peroxide is employed.

14. A process according to claim 5 wherein acid comprises acetic acid.

15. A process according to claim 6 wherein said nitrile comprises acrylonitrile.

* * * * *

UNITED STATES PATENT AND TRADEMARK OFFICE
CERTIFICATE OF CORRECTION

PATENT NO. : 5,364,982

DATED : November 15, 1994

INVENTOR(S) : BROWN et al.

It is certified that error appears in the above-identified patent and that said Letters Patent is hereby corrected as shown below:

Title Page, Item [30], the Serial no. of the first listed United Kingdom Application should be --9103323.3--.

Column 8, lines 29,31,38,41,44,52,59,63, and 66:
   Claims 2, 3, 5, 6, 7, 9, 10, 11 and 12, in the first line of each claim, after "Claim 1" insert --or 13--.

Signed and Sealed this

Fourth Day of April, 1995

Attest:

BRUCE LEHMAN

*Attesting Officer*        *Commissioner of Patents and Trademarks*